(12) United States Patent
Kornbluth et al.

(10) Patent No.: US 11,579,085 B2
(45) Date of Patent: Feb. 14, 2023

(54) SENSING DEVICES

(71) Applicant: Robert Bosch GmbH, Stuttgart (DE)

(72) Inventors: Mordechai Kornbluth, Brighton, MA (US); Kaushal Sagar, Singapore (SG); Shilpa Pant, Singapore (SG)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/931,855

(22) Filed: Jul. 17, 2020

(65) Prior Publication Data

US 2022/0018775 A1 Jan. 20, 2022

(51) Int. Cl.
| | |
|---|---|
| *G01N 21/64* | (2006.01) |
| *G01N 33/18* | (2006.01) |
| *G01N 31/22* | (2006.01) |

(52) U.S. Cl.
CPC ....... *G01N 21/6428* (2013.01); *G01N 21/643* (2013.01); *G01N 31/22* (2013.01); *G01N 33/1813* (2013.01); *G01N 33/1853* (2013.01); *G01N 2021/6439* (2013.01)

(58) Field of Classification Search
CPC .. G01N 21/6428; G01N 21/643; G01N 31/22; G01N 33/1853; G01N 2021/6439
See application file for complete search history.

(56) References Cited

U.S. PATENT DOCUMENTS

| | | | |
|---|---|---|---|
| 6,379,969 B1 * | 4/2002 | Mauze ............... | G01N 21/6428 422/82.05 |
| 8,956,875 B2 | 2/2015 | Kahaian et al. | |
| 10,444,249 B2 | 10/2019 | Fukushima et al. | |
| 2004/0121475 A1 * | 6/2004 | Mckechnie ........ | G01N 33/1853 436/73 |
| 2006/0200318 A1 * | 9/2006 | Morishita .......... | G01N 21/6428 702/20 |
| 2014/0295430 A1 * | 10/2014 | Saito .................... | C12Q 1/6804 435/6.11 |

(Continued)

FOREIGN PATENT DOCUMENTS

| | | | | |
|---|---|---|---|---|
| GB | 2412657 A | * | 10/2005 | ............. B82Y 10/00 |
| GB | 2412657 A | | 10/2005 | |

OTHER PUBLICATIONS

Carol Jurchenko and Khalid S. Salaita, "Lighting Up the Force: Investigating Mechanisms of Mechanotransduction Using Fluorescent Tension Probes", 2015, Molecular and Cellular Biology, 35(15) (Year: 2015).*

(Continued)

*Primary Examiner* — Samuel P Siefke
*Assistant Examiner* — Henry H Nguyen
(74) *Attorney, Agent, or Firm* — Brooks Kushman P.C.

(57) ABSTRACT

A sensing device includes a first sensor configured to capture a first analyte in a fluid medium and to generate a first signal in response to capturing the first analyte. The sensing device also includes a second sensor configured to capture a second analyte in the fluid medium and to generate a second signal in response to capturing the second analyte, where the second analyte is different from the first analyte. The sensing device further includes a detector configured to collect the first and second signals to provide a total signal and to calculate a total concentration of the first and the second analyte in the fluid medium based on the total signal.

20 Claims, 2 Drawing Sheets

(56) References Cited

U.S. PATENT DOCUMENTS

| | | | |
|---|---|---|---|
| 2016/0033413 A1* | 2/2016 | Chodavarapu | G01N 21/6428 435/288.7 |
| 2017/0362648 A1* | 12/2017 | Hassibi | C12Q 1/6834 |
| 2019/0000364 A1* | 1/2019 | Balaconis | G01N 21/6428 |
| 2020/0033313 A1* | 1/2020 | Meeusen | G01N 33/18 |
| 2020/0033314 A1* | 1/2020 | Schwabacher | C09B 29/3673 |

OTHER PUBLICATIONS

Cherkas et al., "Measurement of intracellular concentration of fluorescently-labeled targets in living cells", PLoS One, 2018, 13(4) (Year: 2018).*
Qi et al., "Fluorescent pH Sensors for Broad-Range pH Measurement Based on a Single Fluoraphore", American Chemical Society, Apr. 20, 2015, DOI: 10.1021/acs.analchem.5b00053, Anal. Chem. 2015, 87, 5897-5904, 8 pages.
Daly et al., "Current developments in fluorescent PET (photoinduced electron transfer) sensors and switches", Chem. Soc. Rev., 2015, 44, 4203, DOI: 10.1039/c4cs00334a, Oct. 6, 2014, 11 pages.
Carter et al., "Fluorescent Sensors for Measuring Metal Ions in Living Systems", dx.doi.org/10.1021/cr400546e, Chem. Rev. 2014, 114, 4564-4601, 38 pages.
Jurchenko et al., "Lighting Up the Force: Investigating Mechanisms of Mechanotransduction Using Fluorescent Tension Probes," Molecular and Cellular Biology, Aug. 2015, vol. 35, No. 15, pp. 2570-2582, DOI: 10.1128/MCB.00195-15.
Laidler, "The Entropies of Ion in Aqueous Solution," Canadian Journal of Chemistry, Aug. 1956, vol. 34, No. 8, pp. 1107-1113, https://dx.doi.org/10.1139/v56-144.
Poisson et al., "Diffusion Coefficients of Major Ions in Seawater," Marine Chemistry, 1983, vol. 13, pp. 265-280.

* cited by examiner

SENSING DEVICES

TECHNICAL FIELD

The present disclosure relates to sensing devices, for example, a sensing device configured to sense analytes in an aqueous solution.

BACKGROUND

Calcium (Ca) and magnesium (Mg) ions are generally responsible for the hardness of water. Elevated levels of $Ca^{2+}$ and $Mg^{2+}$ ions in water affect the performance and maintenance of appliances contacting the water. Efficiently detecting and monitoring a total hardness of water may be beneficial to a user, such as helping the user maintain water quality and improve the performance of appliances.

SUMMARY

According to one embodiment, a sensing device is disclosed. The sensing device may include a first sensor configured to capture a first analyte in a fluid medium and to generate a first signal in response to capturing the first analyte. The sensing device may further include a second sensor configured to capture a second analyte in the fluid medium and to generate a second signal in response to capturing the second analyte. The second analyte is different from the first analyte. The sensing device may also include a detector configured to collect the first and the second signal to provide a total signal and to calculate a total concentration of the first and the second analyte in the fluid medium based on the total signal.

According to another embodiment, a sensing device is disclosed. The sensing device may include a sensor film including a mixture of sensors. The mixture of sensors may include first and second sensors. The first and second sensors may be mixed by a mixing ratio. Each of the first and second sensors may be configured to capture an analyte in a fluid medium having at least one analyte and to generate a signal in response to capturing the analyte. The sensing device may further include a detector configured to collect signals from each of the first and second sensors upon each of the first and second sensors capturing one of the at least one analyte in the fluid medium to provide a total signal and to calculate a total concentration of the at least one analyte in the fluid medium based on the total signal.

According to yet another embodiment, a sensing device is disclosed. The sensing device may include a sensor film including a mixture of sensors. The mixture of sensors may include first and second sensors. The first and second sensors may be mixed by a mixing ratio. Each of the first and second sensors may be configured to capture an analyte in a fluid medium and to generate a signal in response to capturing the analyte. The sensing device may further include a first detector configured to collect a first signal having a first frequency from at least one of the first and second sensors in the sensor film upon the at least one of the first and second sensors capturing a first analyte in the fluid medium and to calculate a first total concentration of the first analyte in the fluid medium based on the first signal. The sensing device may also include a second detector configured to collect a second signal having a second frequency from at least another one of the first and second sensors in the sensor film upon the at least another one of the first and second sensors capturing a second analyte in the fluid medium and to calculate a second total concentration of the second analyte in the fluid medium based on the second signal. The second frequency is different from the first frequency.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for applications or implementations.

This present disclosure is not limited to the specific embodiments and methods described below, as specific components and/or conditions may, of course, vary. Furthermore, the terminology used herein is used only for the purpose of describing embodiments of the present disclosure and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description and does not necessarily preclude chemical interactions among constituents of the mixture once mixed.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

The term "substantially" may be used herein to describe disclosed or claimed embodiments. The term "substantially" may modify any value or relative characteristic disclosed or claimed in the present disclosure. "Substantially" may signify that the value or relative characteristic it modifies is within ±0%, 0.1%, 0.5%, 1%, 2%, 3%, 4%, 5% or 10% of the value or relative characteristic.

Reference is being made in detail to compositions, embodiments, and methods of embodiments known to the inventors. However, it should be understood that disclosed embodiments are merely exemplary of the present disclosure which may be embodied in various and alternative forms. Therefore, specific details disclosed herein are not to be interpreted as limiting, rather merely as representative bases for teaching one skilled in the art to variously employ the present disclosure.

Hard water typically contains cations, such as calcium ions ($Ca^{2+}$) and magnesium ions ($Mg^{2+}$), which can form deposits, such as calcium carbonate ($CaCO_3$), in water. Such deposits may form more easily in a hot water system, such as a heat exchanger or a steam oven, where $Ca^{2+}$ and $Mg^{2+}$ ions may react with carbon dioxide at high temperatures to generate the deposits. Because the deposits are thermally insulating, the formation of the deposits adversely affect thermal flows, leading to poor heat transfer in the hot water system.

The total hardness of water is the measurement of the concentration of divalent ions (e.g. $Ca^{2+}$ and $Mg^{2+}$ ions) in the water, typically expressed as milligrams per liter (mg/L) or parts per million (ppm) of $CaCO_3$. The total hardness of water can also be referred to as "degrees of general hardness" (dGH), or "degrees of German hardness", where 1 dGH corresponds to 17.848 ppm $CaCO_3$.

Ion sensing is applicable to the determination of the total hardness of water. For example, fluorescence-based detection methods have been utilized to sense ions (e.g. metal ions) in water, where an ion binds to a detecting molecule to either generate or quench fluorescence. Measurement of the fluorescence can subsequently determine the concentration of the ion in the water. However, because different ions have different sizes and require different binding energies when binding to different detecting molecules, the conventional fluorescence-based detection methods may thus exhibit different sensitivities toward the sensing of different ions. Moreover, these methods may only detect one type of ion at a time.

Apart from the fluorescence-based detection methods, water-soluble sensors have also been employed to detect ions in water. However, because the sensors can dissolve in water, this unavoidably brings contaminates into the water, and the sensors are not reusable. Therefore, there is a need to detect ions in an aqueous environment in a more efficient manner.

Aspects of the present disclosure relate to a sensing device that may detect at least one type of analyte in a fluid medium (e.g. water) and that may be used to determine a total hardness and/or a total toxicity of the fluid medium. In one embodiment, the present disclosure relates to a sensing device including two sensors, where each of the two sensors may be configured to detect an analyte in the fluid medium. In another embodiment, the present disclosure relates to a sensing device including a sensor film, where the sensor film further includes a mixture of sensors by a mixing ratio α. In yet another embodiment, the present disclosure relates to a sensing device including a sensor film embedded with a mixture of sensors by a mixing ratio α, and two detectors, where each of the two detectors may be configured to detect signals of specific frequencies.

Figure 1:
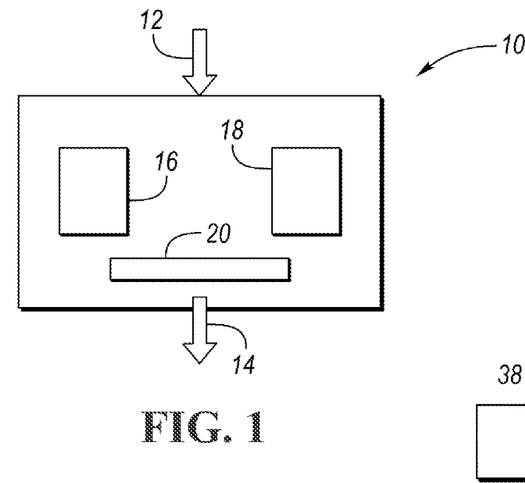
FIG. 1 depicts a schematic diagram of a sensing device according to the present disclosure.

FIG. 1 depicts a schematic diagram of a sensing device according to the present disclosure. The sensing device 10 includes an inlet 12, an outlet 14, a first sensor 16 configured to detect a first analyte in a fluid medium (e.g. water), a second sensor 18 configured to detect a second analyte different from the first analyte in the fluid medium, and a detector 20. The detector 20 may be a photodetector. In one embodiment, the first sensor 16 may be a chemosensor with a first receptor configured to coordinate to the first analyte. Upon coordination by the first analyte, the first sensor 16 may generate a first signal (e.g. fluorescence). Similarly, the second sensor 18 may also be a chemosensor with a second receptor configured to coordinate to the second analyte. Upon coordination by the second analyte, the second sensor 18 may generate a second signal (e.g. fluorescence). The detector 20 may combine the first and second signals to calculate a total signal. Further, the detector 20 may be configured to determine a total concentration of the first and second analytes in the fluid medium based on the total signal.

Apart from chemosensors, the sensing device 10 may also incorporate other types of sensors for analyte detection. Moreover, the sensing device 10 may include more than two sensors such that the sensing device 10 may detect multiple analytes at one time.

In one embodiment, the sensing device 10 may be employed to determine a total hardness of water. As discussed above, $Ca^{2+}$ and $Mg^{2+}$ ions contribute mostly to the total hardness of water. Therefore, in this embodiment, the first sensor 16 may be a chemosensor with a first receptor configured to coordinate to $Ca^{2+}$ ions in the water, and the second sensor 18 may be a chemosensor with a second receptor configured to coordinate to $Mg^{2+}$ ions in the water. After water enters the sensing device 10 via the inlet 12, $Ca^{2+}$ ions in the water may bind to the first receptor of the first sensor 16, generating a first signal (e.g. fluorescence). On the other hand, $Mg^{2+}$ ions in the water may bind to the second receptor of the second sensor 18, generating a second signal (e.g. fluorescence). The detector 20 may gather the first and second signals to obtain a combined signal, which may be subsequently used to calculate a total concentration of the $Ca^{2+}$ and $Mg^{2+}$ ions in the water.

The total hardness of water is substantially proportional to the total concentration of the $Ca^{2+}$ and $Mg^{2+}$ ions in the water. A general formula for calculating the total hardness of water (dGH) is expressed as shown below as formula (1):

$$f(c_{Ca}, c_{Mg}) = dGH = 5.608(c_{Ca} + c_{Mg}) \quad (1)$$

In formula (1), $c_{Ca}$ represents the concentration of $Ca^{2+}$ ions in the water, and $c_{Mg}$ represents the concentration of $Mg^{2+}$ ions in the water, both in units of mmol/L. Therefore, based on a total concentration of the $Ca^{2+}$ and $Mg^{2+}$ ions in the water, the total hardness of the water can be calculated according to formula (1).

In another embodiment, the sensing device 10 may be used to analyze a total toxicity of water. The total toxicity of water may be due to the presence of heavy metal ions in water, such as lead ions ($Pb^{2+}$), mercury ions ($Hg^{2+}$), cadmium ions ($Cd^{2+}$), or arsenic ions ($As^{3+}$ or $As^{5+}$). Therefore, in this embodiment, the first sensor 16 may be a chemosensor with a first receptor configured to coordinate to $Pb^{2+}$ ions in the water, and the second sensor 18 may be a chemosensor with a second receptor configured to coordinate to $Hg^{2+}$ ions in the water. Similarly, when water flows through the sensing device 10, $Pb^{2+}$ and $Hg^{2+}$ ions in the water may bind to the first and second receptors, respectively, and signals (e.g. fluorescence) may be generated from each of the first and second sensors, 16 and 18, upon the bindings. A combined signal may be obtained by the detector 20. Analyzing the combined signal may thus indicate the total toxicity of the $Pb^{2+}$ and $Hg^{2+}$ ions in the water.

In yet another embodiment, the sensing device 10 may include more than two sensors, for example, four sensors, for the detection of a total toxicity of water. In this embodiment, each of the $Pb^{2+}$, $Hg^{2+}$, $Cd^{2+}$, and $As^{3+}$ ions in water may coordinate to a corresponding sensor of the sensing device 10. Likewise, after the detector gathers a total signal generated by each sensor, the total toxicity of the water may thus be determined.

Figure 2:
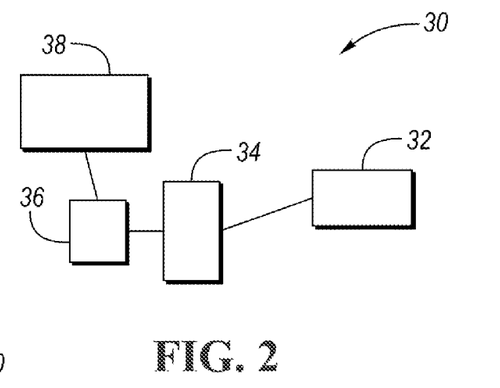
FIG. 2 depicts a schematic diagram of a chemosensor configured to be used in the sensing system described in FIG. 1.

FIG. 2 depicts a schematic diagram of a chemosensor 30 configured to be used in the sensing system 10 described in FIG. 1. As shown in FIG. 2, the chemosensor 30 is a receptor/spacer/fluorophore-type sensor. Specifically, the chemosensor 30 may be linked to a tethering matrix via an anchor 32 thereof. The tethering matrix may include, but not limited to, cellulose microparticles, cellulose films, polymethyl methacrylate (PMMA), polystyrene (PS) microparticles, polyethylene terephthalate (PET) layers, or silicone. The tethering matrix may have a size in a range of 1 to 100 μm and may be embedded within hydrogels. The hydrogels may be, but not limited to, polyurethane or poly(2-hydroxyethyl methacrylate) (Poly-HEMA). In addition, the tethering matrix and the hydrogels may be supported by a polymer support. The polymer support may be, but not limited to, PET.

Still referring to FIG. 2, the chemosensor also includes a fluorophore 34 bound to the anchor 32, and a spacer 36 bound to the fluorophore 34. The fluorophore 34 may be, but not limited to, anthracene, benzene, carbazole, diphenylfurane, naphthalene, 1,8-naphthalimide, N,N,N',N'-tetramethylbenzidine, porphyrin, or pyrene. The spacer 36 may be, but not limited to, methylamine and ethylamine. Further, the chemosensor 30 includes a receptor 38 bound to the spacer 36, where the receptor 38 may coordinate to analytes (e.g. ions) for analyte detection.

Figure 3:
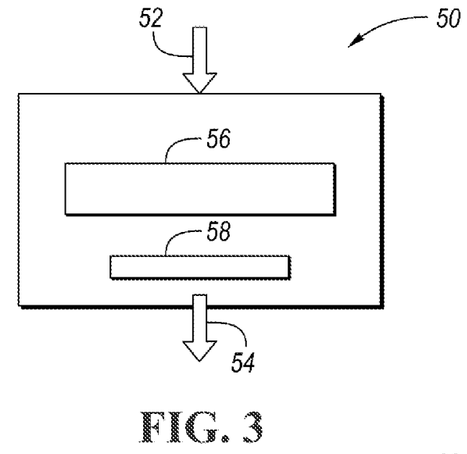
FIG. 3 depicts a schematic diagram of another sensing device according to the present disclosure.

FIG. 3 depicts a schematic diagram of another sensing device according to the present disclosure. The sensing device 50 includes an inlet 52, an outlet 54, a sensor film 56, and a detector 58. The detector 58 may be a photodetector. Further, the sensor film 56 may include a mixture of sensors embedded therein, where the sensors are mixed by a variable mixing ratio α. The mixing ratio α may be in a range of 0.05 and 0.95. Further, by adjusting the mixing ratio α, a total signal collected by the detector 58 may depend substantially on a total concentration of the detected analytes in a fluid medium (e.g. water).

In order for the total signal to depend substantially on the total concentration of the detected analytes, the mixing ratio α needs to be defined when fabricating the sensing device 50. Now, methods for defining the mixing ratio α are described. As a non-limiting example, the sensors described hereafter is a chemosensor as illustrated in FIG. 2. The methods described hereafter may also be applicable when other types of sensors are employed in manufacturing the sensing device 50.

First, a situation where a sensor includes one receptor which can bind to one analyte is described. Suppose that an analyte A may bind to a receptor R in an aqueous solution, forming a chemical entity AR. In the aqueous solution, the concentration of the chemical entity AR, [AR], is in an equilibrium with the concentration of the analyte A, [A], and the concentration of the receptor R, [R]. A general reaction is depicted below as reaction (2):

$$AR \leftrightharpoons A+R \qquad (2)$$

In addition, the binding strength between the analyte A and the receptor R relates to a dissociation constant $K_d$ of the binding, which is defined as formula (3):

$$K_d = c^0 e^{\Delta G/k_B T} \qquad (3)$$

In formula (3), $c^0$ is a reference concentration, $\Delta G$ is the Gibbs free energy of the binding, $k_B$ is the Boltzmann constant, and T is an absolute temperature.

Referring to reaction (2), the dissociation constant $K_d$ of the binding between the analyte A and the receptor R is therefore expressed as stated below as formula (4):

$$K_d = \frac{[A][R]}{[AR]} \qquad (4)$$

Alternatively, formula (4) may be represented as formula (5):

$$K_d = \frac{[c_1][c_{unb}]}{[c_b]} \qquad (5)$$

In formula (5), $c_1$ is the concentration of the analyte A in the aqueous solution, $c_{unb}$ is the concentration of the receptor R not bound by the analyte A, and $c_b$ is the concentration of the receptor R bound by the analyte A.

Further, upon binding, the sensor may generate a signal (e.g. fluorescence). The signal can be given by the following formula (6):

$$\text{signal} = \frac{s_1 c_b + s_0 c_{unb}}{c_b + c_{unb}} \qquad (6)$$

In formula (6), $s_1$ is the signal when the receptor R is bound by the analyte A, and $s_0$ is the signal when the receptor R is in an unbound state (i.e. not bound by the analyte A). In one example, $s_1 = 100 s_0$.

Based on formula (6), the relative signal signal/$s_0$ can be expressed as stated below:

$$\frac{\text{signal}}{s_0} = \frac{\frac{s_1}{s_0} c_b + c_{unb}}{c_b + c_{unb}} \qquad (7)$$

Therefore, according to formula (5), formula (7) can be transformed into the following formula (8):

$$\frac{\text{signal}}{s_0} = \frac{1 + \frac{c_1 s_1}{K_d s_0}}{1 + \frac{c_1}{K_d}} \qquad (8)$$

Figure 4:
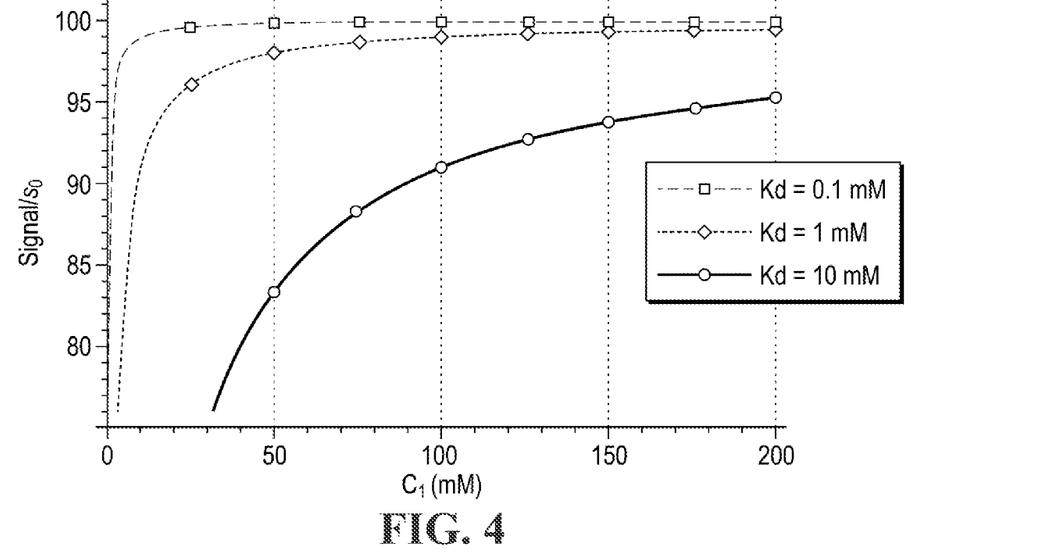
FIG. 4 depicts a graph including three titration curves of signal/$s_0$ as a function of the concentration of the analyte A ($c_1$) for three different dissociation constants.

FIG. 4 depicts three titration curves of signal/$s_0$ as a function of the concentration of the analyte A ($c_1$) for three different dissociation constants. As shown in FIG. 4, for a specific concentration of the analyte A ($c_1$), a higher value $K_d$ corresponds to a lower relative signal (signal/$s_0$) value. Typically, the titration curve measurement is chosen for $K_d$ to be close to the concentration of interest.

Next, the situation where a sensor includes one receptor which can bind to two different analytes is described. Suppose that a receptor R is cross-receptive between two different analytes, analyte $A_1$ and analyte $A_2$. In this situation, the receptor R may have three different states, (a) an unbound state, (b) bound by analyte $A_1$, and (c) bound by analyte $A_2$. Therefore, upon binding, a total signal from the receptor R, following the logic of formula (8), can be expressed as described below:

$$signal_R/s_0 = \frac{1 + \frac{c_1 s_1}{K_d^{A_1 s_0}} + \frac{c_2 s_2}{K_d^{A_2 s_0}}}{1 + \frac{c_1}{K_d^{A_1}} + \frac{c_2}{K_d^{A_2}}} \quad (9)$$

In formula (9), $c_1$ is the concentration of the analyte $A_1$ in the aqueous solution, $c_2$ is the concentration of the analyte $A_2$ in the aqueous solution, $K_d^{A_1}$ is the dissociation constant of the binding between the receptor R and the analyte $A_1$, $K_d^{A_2}$ is the dissociation constant of the binding between the receptor R and the analyst $A_2$, $s_1$ is the signal when the receptor R is bound by the analyte $A_1$, $s_2$ is the signal when the receptor R is bound by the analyte $A_2$, and $s_0$ is the signal when the receptor R is in the unbound state. In one example, $s_2 = s_1 = 100 s_0$.

Furthermore, using the logic of formula (9), if the receptor R can bind to multiple analytes (i.e. more than two analytes), a total signal from the receptor R due to the binding of the analytes is accordingly expressed as described below, where i represents the index over the analytes:

$$signal_R/s_0 = \frac{1 + \sum_i \frac{c_i s_i}{K_d^{A_i s_0}}}{1 + \sum_i \frac{c_i}{K_d^{A_i}}} \quad (10)$$

Referring again to FIG. 3, the sensor film 56 may include a mixture of sensors in a variable mixing ratio $\alpha$, and each of the sensors may include a receptor configured to coordinate to an analyte in a fluid medium. Therefore, upon binding, the total signal of the sensing device 50 is the sum of signals from each of the sensors embedded in the sensor film 56. Based on formula (10), such a total signal can be given as described below:

$$signal = \sum_a \alpha_a * signal_a = \sum_a \alpha_a * \frac{1 + \sum_i \frac{c_i s_i}{K_d^{a i s_0}}}{1 + \sum_i \frac{c_i}{K_d^{a i}}} \quad (11)$$

In formula (11), $\alpha$ represents the number of sensors embedded in the sensor film 56, $signal_a$ represents the normalized signal generated by one of the sensors embedded in the sensor film 56, and $\alpha_a$ represents the ratio of the amount of the one of the sensors embedded in the sensor film 56 to the total amount of the sensors embedded in the sensor film 56.

To obtain an optimal value of $\alpha_a$, the absolute gradient of a signal shall be maximized with respect to the quantity of interest and minimized with respect to all conjugate quantities. For example, in an embodiment where a sensing device is used to determine a total hardness of water, the total hardness of water is substantially proportional to a total concentration of the $Ca^{2+}$ and $Mg^{2+}$ ions, $c_{Ca} + c_{Mg}$, in the water. As such, an optimal value of $\alpha_a$ may be determined using the following mathematical formulas (12) and (13):

$$\arg_\alpha \max \left| \frac{d(\text{signal})}{d(c_{Ca} + c_{Mg})} \right| \quad (12)$$

$$\arg_\alpha \min \left| \frac{d(\text{signal})}{d(c_{Ca} - c_{Mg})} \right| \quad (13)$$

In one embodiment, the sensor film 56 of the sensing device 50 may include a first sensor configured to detect a first analyte ($A_1$) in a fluid medium (e.g. water) and a second sensor configured to detect a second analyte ($A_2$) in the fluid medium, where the second analyte ($A_2$) is different from the first analyte ($A_1$). The first and second sensors are mixed in the sensor film 56 by a mixing ratio $\alpha$. The mixing ratio $\alpha$ may be in a range of 0.05 and 0.95.

Specifically, the first sensor may be a chemosensor with a first receptor configured to selectively coordinate to the first analyte ($A_1$). Upon coordination by the first analyte ($A_1$), the first sensor may generate a first signal (e.g. fluorescence). In addition, the second sensor may be a chemosensor with a second receptor configured to selectively coordinate to the second analyte ($A_2$). Upon coordination by the second analyte ($A_2$), the second sensor may generate a second signal (e.g. fluorescence). The detector may combine the first and second signals to provide a total signal. According to formula (14), the total signal can be expressed as stated below:

$$\text{signal} = \frac{1 + \frac{c_1 s_1}{K_d^{A_1 s_0}}}{1 + \frac{c_1}{K_d^{A_1}}} + \alpha \frac{1 + \frac{c_2 s_2}{K_d^{A_2 s_0}}}{1 + \frac{c_2}{K_d^{A_2}}} \quad (14)$$

In formula (14), $c_1$ is the concentration of the analyte $A_1$ in the fluid medium, $c_2$ is the concentration of the analyte $A_2$ in the fluid medium, $K_d^{A_1}$ is the dissociation constant of the binding between the first receptor and the first analyte $A_1$, $K_d^{A_2}$ is the dissociation constant of the binding between the second receptor and the second analyte $A_2$, $s_1$ is the signal when the first receptor is bound by the first analyte $A_1$, $s_2$ is the signal when the second receptor is bound by the second analyte $A_2$, and $s_0$ is the signal when the first and second receptors are not bound by the first and second analytes, $A_1$ and $A_2$. In one example, $s_2 = s_1 = 100 s_0$.

When applying the sensing device 50 to the determination of a total hardness of water, the first sensor may be a chemosensor with a first receptor configured to coordinate to $Ca^{2+}$ ions in the water, and the second sensor may be a chemosensor with a second receptor configured to coordinate to $Mg^{2+}$ ions in the water. To make the total signal depend substantially on a total concentration of the $Ca^{2+}$ and $Mg^{2+}$ ions in the water, a mixing ratio $\alpha$ of the first and second sensors may be determined, using formula (12) and (13), when fabricating the sensor film 56. Suppose the water is rich in $Ca^{2+}$ ions and that the total hardness (dGH) of a sample water is around 5. Further, in formula (14), suppose $s_2 = s_1 = 100 s_0$, and that the dissociation constants for the first and second sensors, $K_d^{A_1}$ and $K_d^{A_2}$, are both 1 mM. Using formulas (12) and (13), an optimal mixing ratio $\alpha=0.65$ may therefore be calculated. With the mixing ratio $\alpha=0.65$, the total signal of the sensing device 50 may be substantially proportional to the total concentration of the $Ca^{2+}$ and $Mg^{2+}$ ions in the water. The total signal may not be affected substantially by the individual concentration of the $Ca^{2+}$ or $Mg^{2+}$ ions in the water so long as the total concentration of the $Ca^{2+}$ and $Mg^{2+}$ ions in the water remains substantially the same.

Figure 5:
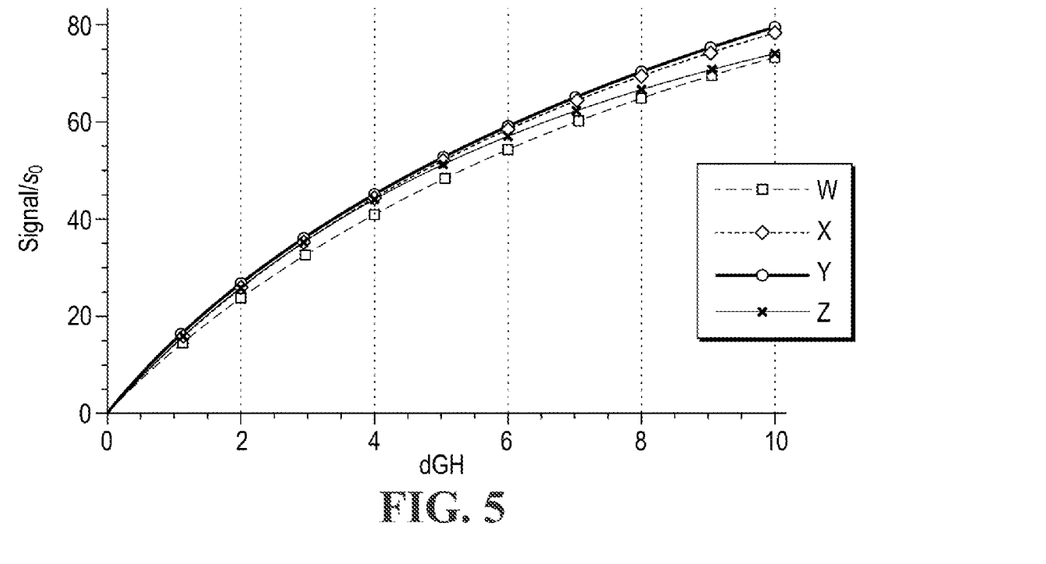
FIG. 5 depicts a graph of titration curves of signal/$s_0$ as a function of the total hardness of water (dGH).

FIG. 5 depicts titration curves of signal/$s_0$ as a function of the total hardness of water (dGH), when $s_2=s_1=100$ $s_0$, and the dissociation constants for the first and second sensors, $K_d^{A1}$ and $K_d^{A2}$, are both 1 mM. In FIG. 5, the titration curves represent situations where a total concentration of the $Ca^{2+}$ and $Mg^{2+}$ ions in the water are substantially the same. However, each of the titration curves corresponds to a different fraction of the individual concentration of $Ca^{2+}$ ions to the individual concentration of $Mg^{2+}$ ions in the water. The titration curve W corresponds to a situation where the fraction of the individual concentration of $Ca^{2+}$ ions to the individual concentration of $Mg^{2+}$ ions in the water is 0.5. The titration curve X corresponds to a situation where the fraction of the individual concentration of $Ca^{2+}$ ions to the individual concentration of $Mg^{2+}$ ions in the water is 1. The titration curve Y corresponds to a situation where the fraction of the individual concentration of $Ca^{2+}$ ions to the individual concentration of $Mg^{2+}$ ions in the water is 2. The titration curve Z corresponds to a situation where the fraction of the individual concentration of $Ca^{2+}$ ions to the individual concentration of $Mg^{2+}$ ions in the water is 6.

Referring to FIG. 5, although the fractions of the individual concentration of $Ca^{2+}$ ions to the individual concentration of $Mg^{2+}$ ions of each titration curve are different, a specific relevant signal (signal/$s_0$) value, however, may correspond to a dGH with minimal deviations (e.g. around 5%). For example, if the sensing device determines a relevant signal (signal/$s_0$) value of 60, the sensing device may then provide the total hardness of water (dGH) as 6 (or closely around 6). Similarly, if the sensing device determines a relevant signal (signal/$s_0$) value of 40, the sensing device may then indicate the total hardness of water (dGH) as 3.5 (or closely around 3.5).

The sensing device 50 described in FIG. 3 may also be employed to analyze a total toxicity of water. As mentioned above, the total toxicity of water may be due to the presence of heavy metal ions, such as $Pb^{2+}$, $Hg^{2+}$, $Cd^{2+}$, $As^{3+}$, or $As^{5+}$ ions. Therefore, in this embodiment, the sensor film 56 of the sensing device 50 may include a first sensor and a second sensor, where the first and second sensors are embedded in the sensor film 56 by a mixing ratio $\alpha$. Specifically, the first sensor may be a chemosensor with a first receptor configured to coordinate to $Pb^{2+}$ ions in the water, and the second sensor may be a chemosensor with a second receptor configured to coordinate to $Hg^{2+}$ ions in the water. To make the total signal depend substantially on a total concentration of the $Pb^{2+}$ and $Hg^{2+}$ ions, an optimal mixing ratio $\alpha$ may be defined, using the formulas (12) and (13), when fabricating the sensor film 56. With the optimal mixing ratio $\alpha$, the total signal provided by the sensing device 50 is substantially proportional to the total toxicity of the water. Therefore, the total toxicity of the water may be determined based on the total signal.

Moreover, if the sensing device 50 includes more than two sensors, for example, four sensors, embedded in the sensor film 56 by a mixing ratio $\alpha$, each of the $Pb^{2+}$, $Hg^{2+}$, $Cd^{2+}$, and $As^{3+}$ ions may coordinate to a corresponding sensor in the sensor film 56. Likewise, because the total signal obtained from all the four sensors depends substantially on a total concentration of the $Pb^{2+}$, $Hg^{2+}$, $Cd^{2+}$, and $As^{3+}$ ions in the water, the total toxicity of the water may therefore be determined based on the total signal.

Figure 6:
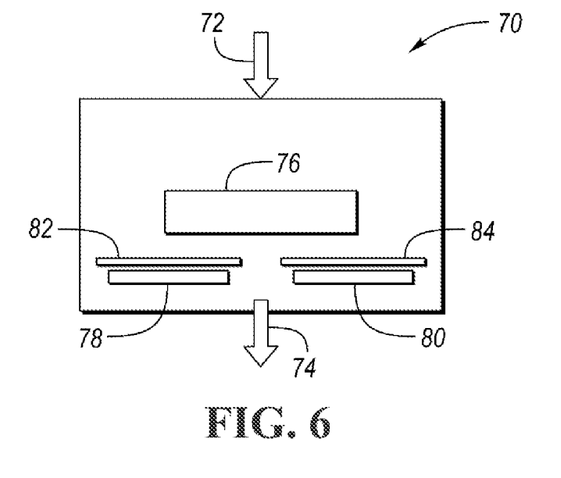
FIG. 6 depicts a schematic diagram of yet another sensing device according to the present disclosure.

Apart from a sensing device having one detector that collects signals of different frequency values, the sensing device may include more than one detector such that each detector may collect signals of corresponding frequency values. FIG. 6 depicts a schematic diagram of yet another sensing device according to the present disclosure. Specifically, the sensing device 70 includes an inlet 72, an outlet 74, a sensor film 76, a first detector 78, and a second detector 80. The first and second detectors, 78 and 80, may be photodetectors. Further, the sensor film 76 may include a mixture of sensors embedded therein, where the sensors are mixed by a variable mixing ratio $\alpha$. The mixing ratio $\alpha$ may be in a range of 0.05 and 0.95.

In one embodiment, the sensing device 70 may be used to simultaneously determine a total hardness of water and a total toxicity of the water. Referring to FIG. 6, the sensor film 76 may include a first sensor and a second sensor, where the first and second sensors are mixed in the sensor film 76 by a mixing ratio $\alpha$. Specifically, the first sensor may be a chemosensor with a first receptor configured to coordinate to $Ca^{2+}$ ions in the water. Upon binding by the $Ca^{2+}$ ions, the first sensor may generate a first signal (e.g. fluorescence) with a first frequency. In this embodiment, the first signal may be collected by the first detector 78, where the total hardness of water may be determined based on the first signal. Similarly, the second sensor may be a chemosensor with a second receptor configured to coordinate to $Pb^{2+}$ ions in the water. Upon binding by the $Pb^{2+}$ ions, the second sensor may generate a second signal (e.g. fluorescence) with a second frequency. Accordingly, the second signal may be received by the second detector 80, where the total toxicity of the water may be calculated based on the second signal.

To better achieve this purpose, a first filter 82 may be positioned between the sensor film 76 and the first detector 78. The first filter 82 is configured to filter out the second signal. In addition, a second filter 84 may be positioned between the sensor film 76 and the second detector 80. Similarly, the second filter 84 is configured to filter out the first signal.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A sensing device comprising:
    a first sensor having a first receptor capturing a first analyte ($A_1$) in a fluid medium at a $c_1$ concentration generating a first signal $s_1$ when the first receptor is bound by the first analyte;
    a second sensor having a second receptor capturing a second analyte ($A_2$) in the fluid medium at a $c_2$ concentration generating a second signal $s_2$ when the second receptor is bound by the second analyte, the second analyte being different from the first analyte, the first and second sensors present to each other in a mixing ratio ($\alpha$); and
    a detector comprising a processor programmed to perform the step of solving for the mixing ratio ($\alpha$) using the following equations:

$$\text{signal} = \frac{1 + \frac{c_1 s_1}{K_d^{A_1} s_0}}{1 + \frac{c_1}{K_d^{A_1}}} + \alpha \frac{1 + \frac{c_2 s_2}{K_d^{A_2} s_0}}{1 + \frac{c_2}{K_d^{A_2}}},$$

$$\arg_\alpha \max \left| \frac{d(\text{signal})}{d(c_1 + c_2)} \right|, \text{ and } \arg_\alpha \min \left| \frac{d(\text{signal})}{d(c_1 - c_2)} \right|$$

where $K_d^{A_1}$ is a dissociation constant of the binding between the first receptor and the first analyte $A_1$, $K_d^{A_2}$ is a dissociation constant of the binding between the second receptor and the second analyte $A_2$, $s_0$ is the signal when the first and second receptors are not bound by the first and second analytes, $A_1$ and $A_2$, respectively; and
    the processor of the detector further programmed to collect the first signal $s_1$ and the second signal $s_2$ to calculate a total signal and a total concentration of the first analyte ($A_1$) and the second analyte ($A_2$) in the fluid based on the total signal and the mixing ratio ($\alpha$).

2. The sensing device of claim 1 further comprising a first spacer, a first fluorophore, and a first anchor, the first spacer is bound to the first receptor, the first fluorophore is bound to the first spacer, and the first anchor is bound to the first fluorophore.

3. The sensing device of claim 2, wherein the first fluorophore is selected from the group consisting of anthracene, benzene, carbazole, diphenylfurane, naphthalene, 1,8-naphthalimide, N,N,N',N'-tetramethylbenzidine, porphyrin, and pyrene.

4. The sensing device of claim 2, wherein the first sensor is linked to a tethering matrix via the first anchor, the tethering matrix embedded with hydrogels.

5. The sensing device of claim 4, wherein the hydrogels are polyurethane or poly(2-hydroxyethyl methacrylate) (Poly-HEMA).

6. The sensing device of claim 1 further comprising a second spacer, a second fluorophore, and a second anchor, the second spacer is bound to the second receptor, the second fluorophore is bound to the second spacer, and the second anchor is bound to the second fluorophore.

7. The sensing device of claim 6, wherein the second fluorophore is selected from the group consisting of anthracene, benzene, carbazole, diphenylfurane, naphthalene, 1,8-naphthalimide, N,N,N',N'-tetramethylbenzidine, porphyrin, and pyrene.

8. The sensing device of claim 6, wherein the second sensor is linked to a tethering matrix via the second anchor, the tethering matrix embedded with hydrogels.

9. The sensing device of claim 8, wherein the hydrogels are polyurethane or poly(2-hydroxyethyl methacrylate) (Poly-HEMA).

10. A sensing device comprising:
    a sensor film having a mixture of sensors, the mixture of sensors including first and second sensors, the first and second sensors present to each other in a mixing ratio ($\alpha$), the first sensor having a first receptor capturing a first analyte ($A_1$) in a fluid medium at a $c_1$ concentration generating a first signal $s_1$ when the first receptor is bound by the first analyte and the second sensor having a second receptor capturing a second analyte ($A_2$) in the fluid medium at a $c_2$ concentration generating a second signal $s_2$ when the second receptor is bound by the second analyte, the sensor film generating a signal in response to the first sensor capturing the first analyte and the second sensor capturing the second analyte; and
    a detector comprising a processor programmed to perform the step of solving for the mixing ratio ($\alpha$) is solved using the following equations:

$$\text{signal} = \frac{1 + \frac{c_1 s_1}{K_d^{A_1} s_0}}{1 + \frac{c_1}{K_d^{A_1}}} + \alpha \frac{1 + \frac{c_2 s_2}{K_d^{A_2} s_0}}{1 + \frac{c_2}{K_d^{A_2}}},$$

$$\arg_\alpha \max \left| \frac{d(\text{signal})}{d(c_1 + c_2)} \right|, \text{ and } \arg_\alpha \min \left| \frac{d(\text{signal})}{d(c_1 - c_2)} \right|$$

where $K_d^{A_1}$ is a dissociation constant of the binding between the first receptor and the first analyte $A_1$, $K_d^{A_2}$ is a dissociation constant of the binding between the second receptor and the second analyte $A_2$, $s_0$ is the signal when the first and second receptors are not bound by the first and second analytes, $A_1$ and $A_2$, respectively; and
    the processor of the detector further programmed to collect the first signal $s_1$ and the second signal $s_2$ to calculate a total signal and a total concentration of the first analyte ($A_1$) and the second analyte ($A_2$) in the fluid based on the total signal and the mixing ratio ($\alpha$).

11. The sensing device of claim 10 further comprising a first spacer, a first fluorophore, and a first anchor, the first spacer is bound to the first receptor, the first fluorophore is bound to the spacer, and the first anchor is bound to the first fluorophore.

12. The sensing device of claim 11, wherein the fluorophore is selected from the group consisting of anthracene, benzene, carbazole, diphenylfurane, naphthalene, 1,8-naphthalimide, N,N,N',N'-tetramethylbenzidine, porphyrin, and pyrene.

13. A sensing device comprising:
    a sensor film having a mixture of sensors, the mixture of sensors including first and second sensors, the first and second sensors present to each other in a mixing ratio ($\alpha$), the first sensor having a first receptor capturing a first metal ion analyte ($A_1$) in a fluid medium at a $c_1$ concentration generating a first signal $s_1$ when the first receptor is bound by the first metal ion analyte and the second sensor having a second receptor capturing a second metal ion analyte of ($A_2$) in the fluid medium at a $c_2$ concentration generating a second signal $s_2$ when the second receptor is bound by the second metal ion analyte, the mixing ratio depending on the first and second metal ion analytes, the sensor film generating a signal in response to the first sensor capturing the first metal ion analyte and the second sensor capturing the second metal ion analyte; and a detector comprising a processor programmed to perform the step of solving for the mixing ratio ($\alpha$) using the following equations:

$$\text{signal} = \frac{1 + \frac{c_1 s_1}{K_d^{A_1 s_0}}}{1 + \frac{c_1}{K_d^{A_1}}} + \alpha \frac{1 + \frac{c_2 s_2}{K_d^{A_2 s_0}}}{1 + \frac{c_2}{K_d^{A_2}}},$$

$$\arg_\alpha \max \left| \frac{d(\text{signal})}{d(c_1 + c_2)} \right|, \text{ and } \arg_\alpha \min \left| \frac{d(\text{signal})}{d(c_1 - c_2)} \right|$$

where $K_d^{A_1}$ is a dissociation constant of the binding between the first receptor and the first metal ion analyte $A_1$, $K_d^{A_2}$ is a dissociation constant of the binding between the second receptor and the second metal ion analyte $A_2$, $s_0$ is the signal when the first and second receptors are not bound by the first and second metal ion analytes, $A_1$ and $A_2$, respectively; and the processor of the detector further programmed to calculate a total concentration of the first metal ion analyte ($A_1$) and the second metal ion analyte ($A_2$) in the fluid medium based on a total signal of first signal $s_1$ and the second signal $s_2$ and the mixing ratio ($\alpha$).

14. The sensing device of claim 13, further comprising a first spacer, a first fluorophore, and a first anchor, the first spacer is bound to the first receptor, the first fluorophore is bound to the first spacer, and the first anchor is bound to the first fluorophore.

15. The sensing device of claim 14, wherein the first fluorophore is selected from the group consisting of anthracene, benzene, carbazole, diphenylfurane, naphthalene, 1,8-naphthalimide, N,N,N',N'-tetramethylbenzidine, porphyrin, and pyrene.

16. The sensing device of claim 14, wherein the first sensor is linked to a tethering matrix via the first anchor, the tethering matrix embedded with hydrogels.

17. The sensing device of claim 16, wherein the hydrogels are polyurethane or poly(2-hydroxyethyl methacrylate) (Poly-HEMA).

18. The sensing device of claim 13 further comprising a second spacer, a second fluorophore, and a second anchor, the second spacer is bound to the second receptor, the second fluorophore is bound to the second spacer, and the second anchor is bound to the second fluorophore.

19. The sensing device of claim 13, wherein the first and second receptors are the same receptor.

20. The sensing device of claim 13, wherein the first metal ion analyte is $Ca^{2+}$ ions and the second metal ion analyte is $Mg^{2+}$ ions.

* * * * *